US006175037B1

(12) United States Patent
Tweedy

(10) Patent No.: US 6,175,037 B1
(45) Date of Patent: Jan. 16, 2001

(54) PROCESS FOR THE PREPARATION OF (METH)ACRYLATE ESTERS AND POLYESTER (METH)ACRYLATES USING MICROWAVE ENERGY AS A HEATING SOURCE

(75) Inventor: Harrell Emmett Tweedy, Acworth, GA (US)

(73) Assignee: UCB, S.A., Brussels (BE)

( * ) Notice: Under 35 U.S.C. 154(b), the term of this patent shall be extended for 0 days.

(21) Appl. No.: 09/168,991

(22) Filed: Oct. 9, 1998

(51) Int. Cl.$^7$ .......................... C07C 69/52; C07C 51/00; C08J 3/28
(52) U.S. Cl. .................. 560/224; 560/205; 560/220; 560/221; 204/157.87; 422/186.29; 522/4; 522/6; 522/135
(58) Field of Search ........................ 560/205, 220, 560/221, 224; 204/157.87; 422/186.29; 522/4, 6, 135

(56) References Cited

U.S. PATENT DOCUMENTS

| 4,739,108 | * | 4/1988 | Lillwitz . | |
|---|---|---|---|---|
| 5,239,017 | | 8/1993 | Pelesko et al. | 525/383 |
| 5,387,397 | | 2/1995 | Strauss et al. | 422/129 |
| 5,498,751 | | 3/1996 | Trapasso et al. | 560/217 |
| 5,554,785 | | 9/1996 | Trapasso et al. | 560/201 |

FOREIGN PATENT DOCUMENTS

| 21 242 | 1/1981 | (EP) . |
|---|---|---|
| 202 610 | 11/1986 | (EP) . |
| 376 090 | 7/1990 | (EP) . |
| 07-330667 | 12/1995 | (JP) . |
| 91 18861 | 12/1991 | (WO) . |

OTHER PUBLICATIONS

Raner et al., *J. Org. Chem.*, 57, 6231–6234 (1992).
Raner et al., *J. Org. Chem.*, 58, 950–953 (1993).
Strauss et al., *Aust. J. Chem.*, 48, 1665–1692 (1995).

* cited by examiner

*Primary Examiner*—James O. Wilson
*Assistant Examiner*—Robert W. Deemie
(74) *Attorney, Agent, or Firm*—Wenderoth, Lind & Ponack, L.L.P.

(57) ABSTRACT

An improved process for preparing acrylate esters, methacrylate esters, polyester acrylates or polyester methacrylates by reacting acrylic or methacrylic acid with a monohydroxy containing compound or a polyhydroxy containing compound in the presence of a catalyst and polymerization inhibitor in a reaction vessel, in the presence or absence of a solvent, under microwave energy as a heating source. Advantages of using microwave energy in place of conventional thermal heating include higher temperatures coupled with shorter residence times, reduced production costs, increased capacity, lower energy costs, effective use of raw materials, and solventless processing which is environmentally friendly.

30 Claims, No Drawings

PROCESS FOR THE PREPARATION OF (METH)ACRYLATE ESTERS AND POLYESTER (METH)ACRYLATES USING MICROWAVE ENERGY AS A HEATING SOURCE

BACKGROUND OF THE INVENTION

1. Field of the Invention

The present invention relates to a process for preparing acrylate esters, methacrylate esters, polyester acrylates or polyester methacrylates by reacting acrylic or methacrylic acid with a monohydroxy containing compound or a polyhydroxy containing compound in a reaction vessel in the presence of a catalyst and polymerization inhibitor.

2. Description of Related Art

Conventionally, methacrylate esters and acrylate esters have been prepared via a direct esterification reaction by reacting methacrylic acid or acrylic acid, usually in excess, with an alcohol or a polyol in the presence of an azeotroping solvent for water removal, typically a hydrocarbon solvent, an esterification catalyst and a polymerization inhibitor. Limited examples are also known where synthesis can also occur in the absence of a hydrocarbon solvent, for example, European Patent Application 0 202 610 by BASF Corporation and European Patent Application 0 376 090 by Henkel Corporation. In addition, (meth)acrylate esters have been prepared using transesterification reaction conditions as described in U.S. Pat. Nos. 5,498,751 and 5,554,785.

In all of the above mentioned patents and published applications, the source of heating is conventional thermal methods, such as placing a heating unit into the reaction mixture or jacketing the reaction vessel and reaction mixture with an external heating source. In conventional thermal methods, the reactants are placed in a vessel, the vessel is heated by conventional thermal methods, and the heat is transferred to the reaction mixture conductively, usually in the presence of a solvent.

Microwaves have been used as an energy source in various esterification reactions where reactants are not prone to undergo further reaction via free radical initiated propagation. For example, U.S. Pat. No. 5,239,017 to Pelesko et al. discloses that anhydride groups of a polymer can be esterified in a cross-linking reaction with a polyol using microwave heating.

A working example in U.S. Pat. No. 5,387,397 to Strauss uses microwave heating to react certain unsaturated acids with an alcohol. This patent also couples the reactor directly to refrigeration for cooling in order to prevent by-product formation or product degradation. Further, water produced by the esterification reaction in the example is not separated from the reaction mixture. The rapid heating and cooling is to prevent decomposition or polymerization of the product, and is disclosed as an advantage. The Strauss patent does not disclose that methacrylic acid or acrylic acid can be esterified using microwaves as the energy source, but only discloses that acids with internal hydrocarbon chain unsaturation, such as crotonic acid, can be esterified. It is well known in the art that internal unsaturation is generally more stable to thermal or free radical induced reactions than terminal unsaturation in unsaturated compounds, such as those terminated with (meth)acrylic functionality.

Raner et al., J. Org. Chem., 57, 6231–6234 (1992), compares the properties and parameters of the esterification reaction of 2,4,6-Trimethylbenzoic Acid with 2-propanol using as a heat source, microwaves, verses a conventional heat source. Raner et al., J. Org. Chem., 58, 950–953 (1993), continues the investigations of the preceding article. These articles do not disclose the esterification of (meth)acrylic acid.

Strauss et al., Aust. J. Chem., 48, 1665–1692 (1995), reviews microwave assisted organic synthesis. On pages 1677–78 of this article, a discussion of the further reaction of a terminally unsaturated acrylate compound using microwaves is presented. This article does not disclose that the particular (meth)acrylic acid or acrylic acid material can be prepared by using a microwave, only that it can be further reacted with additional reactants via microwave energy. Additionally, like the patent to Strauss discussed previously, this article indicates a need to rapidly cool the reaction mixture in order to limit hydrolysis, dimerization and polymerization of the resulting product containing the unsaturation.

BRIEF SUMMARY OF THE INVENTION

Surprisingly, it has been discovered that microwaves can be used in the synthesis of highly reactive compounds which are prepared from acrylic acid or methacrylic acid reactants. These highly reactive compounds are further capable of free radical polymerization via thermal, photochemical or other means of initiation. Synthesis of these reactive products using microwaves as the heating source, can be accomplished without any significant polymerization of the products or of the acrylic acid or methacrylic acid reactants used to prepare the highly reactive compounds. It has thus been discovered that microwaves can be effectively used to synthesize methacrylate esters, acrylate esters, polyester methacrylates and polyester acrylates with certain advantages over conventional synthetic methods.

In a conventional inductive thermal heating process, the reactants are gradually heated as heat penetrates from the outside of the reactor to the reactants inside. In alternative processes, this heating may be supplied from the inside of the reactor, using a heating coil or other conductive heating devices. The heat is gradually absorbed by the reactants and any solvent, solid, or other component in the reactor, which in turn gets warmer and results in the reaction eventually taking place. In contrast, microwave energy is "cold", producing heat only when the energy is absorbed directly by the reaction mixture components that are responsive to microwaves. The reactants which absorb the energy are rapidly heated when exposed to the microwave energy and the energy (as heat) is further distributed directly to the surrounding reaction medium. Because microwaves directly interact with the microwave-responsive molecules of the reactants, thereby generating heat, there is little need for an additional inert liquid or solid medium or additional solvent to convey heat from the heating means to the reactants. Using microwave heating for chemical reactions in place of conventional thermal heating has many advantages including: achieving higher reaction mixture temperatures more rapidly, shorter residence times, reduced production costs, increased capacity utilization of reaction vessels, and lower "waste" in energy utilization. Lower excesses of non-limiting reactants and solventless processing, which are environmentally friendly, are additional important advantages. The process of this invention has an important commercial significance as well as providing technical advantages for synthesis of the highly reactive acrylates and methacrylates over the prior art methods.

DETAILED DESCRIPTION OF THE INVENTION

The invention concerns a process for preparing an acrylate ester, a methacrylic ester, a polyester acrylate, or a polyester methacrylate, comprising reacting acrylic or methacrylic acid with a monohydroxy containing compound or polyhydroxy containing compound in a reaction vessel in the presence of a catalyst under microwave heating.

In the present invention, the term "(meth)acrylic acid" encompasses both acrylic acid and methacrylic acid. Likewise, the term (meth)acrylate encompasses both acrylates and methacrylates and "polyester (meth)acrylate" encompasses both polyester acrylates and polyester methacrylates.

The term "polyester (meth)acrylate" is defined as a (meth)acrylate derived from a polyol, and may have one or more (meth)acrylate functional groups present in the final product.

Microwaves can be generated by any of a variety of methods known in microwave technology. Typically these methods depend upon klystrons or magnetrons to serve as the microwave generation source. Typically, the frequency of generation is in the approximate range of 300 MHz to 30 GHz and the corresponding wavelength of about 1 m to 1 mm. Although any frequency in this range can theoretically be used, more or less effectively, it is preferable to use a frequency within the commercially accessible ranges which include about 850–950 MHz or about 2300–2600 MHz. These frequencies are allocated to non-communication uses by legislation and international conventions. While other frequencies can be used, their use is severely restricted by leakage containment and other regulations to avoid disruption of electronic communications. The preferred frequencies, in the United States, are about 2450 MHz±50MHz or about 915 MHz±13 MHz, since many commercially available microwave units operate at or about these frequencies. In other countries, the preferred frequencies are accordingly adjusted to the frequencies allocated for commercial microwaves. Of course, slight variations of these frequencies will not substantially affect the results of this invention, however, slight variations in other process parameters may have to be made in order to achieve optimum results since molecular response to the microwave frequency is somewhat dependent upon the molecular entity (polarity) and upon the microwave frequency being used to deliver the energy. The variations in the other parameters will be readily apparent to those skilled in the art. The frequency near 2450 MHz is well known in conventional food processing, due to the good response of water and other polar molecules in foods to this frequency range. The same is true for the frequency near 915 MHz where commercial equipment has been developed for higher power generation capabilities. Therefore, in the present invention, the frequency of the microwaves can be between 300 MHz and 30GHz, with the preferred range being between about 850 MHz and about 950 MHz or between about 2300 MHz and 2600 MHz, or more preferably about 915 MHz±13 MHz or about 2450 MHz±50MHz.

Once generated, the microwaves are transferred to the reactants in any of the known conventional methods which include: multimodal, monomodal, variable sweep or other means for delivering the microwaves to the reactants. Containment of the microwaves is generally accomplished by a mechanism which allows the microwaves to impinge on the sample in either a monomodal (essentially single wavecrest impingement) or multimodal (multiple reflections of the same energy wave) process. This impingement can occur either by locating the target sample vessel containing the reactants directly in the wave guide (monomodal) or by directing the microwaves into an enclosed or shielded cavity which prevents their escape into the surrounding environment, but allows them to undergo multiple reflections (multimodal) and eventual interaction with the reactant sample. Frequency sweeping is another method known in the art for delivery of microwaves. These application and containment means are well known in the art. The specific mode of application is not a critical parameter for this invention, although slight adjustments may have to be made as to exposure conditions, duration, etc., to achieve optimum results with the different application modes. These adjustments will be readily apparent to those skilled in the art.

The process of this invention can be used to produce both monoesters and polyester compounds. Monoesters are produced by reacting monohydroxy containing compounds with (meth)acrylic acid. The monohydroxy containing compounds which can be used in the invention include, but are not limited, to $C_{1-18}$ aliphatic monohydroxy compounds which are linear or branched, such as methanol, ethanol, butanol, propanol, isopropanol, octanol, decanol or mixtures of these compounds, and cycloaliphatic monohydroxy compounds such as cyclohexanol or hydroxyethylcyclohexanol. In addition, aromatic monohydroxy compounds such as phenoxyethanol or reaction products of phenol and various amounts of ethylene oxide and/or propylene oxide, can also be used.

Polyester (meth)acrylates are produced by reacting a polyhydroxy containing compound with (meth)acrylic acid. The polyhydroxy containing compounds, also called "polyols", which can be used in the invention include compounds which contain more than one hydroxy group and are also compatible with the reaction conditions. Generally, the polyols which can be used in this invention have 2 to 10 hydroxy groups, preferably have 2 to 6 hydroxy groups and have 2 to about 36 carbon atoms. These polyols include branched and linear aliphatic polyols, cycloaliphatic polyols, aromatic polyols, polyether polyols and polyester polyols. Examples of aliphatic polyols included diols such as ethylene glycol, propylene glycol, butanediol, hexanediol, neopentyl glycol, tripropylene glycol, triethylene glycol, tetraethylene glycol and dimethylolpropane; triols, such as glycerine, trimethylolpropane, ethoxylated trimethylolpropane, propoxylated glycerine and trimethylolethane; tetra-ols, such as pentaerythritol and di-trimethylolpropane and hexa-ols such as dipentaerythritol. Examples of cycloaliphatic polyols include dimethylolcyclohexane. Examples of aromatic polyols include bisphenol A, bisphenol F, reaction products of bisphenol A or bisphenol F, with various amounts of ethylene oxide and propylene oxide. The polyether polyols which can be used in the present invention include both aromatic and aliphatic polyethers. The aliphatic groups of the polyether polyols can be linear, branched or cyclic. Examples of polyether polyols include di and tri glycols, such as diethylene glycol and triethylene glycol, polyethylene glycol, polypropylene glycol and mixed polyethers, such as poly(propylene-ethylene) glycol. Polyester polyols are polyols which have ester linkages. For example, an excess of polyol is reacted with a diacid to produce a low molecular weight compound having about 1 to about 6 ester linkages and reactive hydroxy groups. Any of the aforementioned polyols or combinations of them can be used to prepare the polyester polyols. Examples of the diacids used to produce polyester polyol include: aliphatic, and cycloaliphatic diacids such as succinic acid and adipic acid, and aromatic diacids such as terephthalic acid.

In the process of the present invention, the goal is to produce (meth)acrylate functional products. Therefore, it is desirable to functionalize at least about 5.0% of the hydroxy functionality in the starting hydroxy functional compound with (meth)acrylic acid. Preferably, about 50% to about 100% of the hydroxy functional groups should be functionalized.

Additionally, other reactive groups can be present on the hydroxy functional material provided they are compatible with the esterification process. For example, functional groups including, but not limited to, nitrogen containing functional groups, and oxygen containing functional groups. These groups may or may not be blocked, however, it is preferred that these groups are blocked to prevent these groups from reacting with the acid group of the (meth) acrylic acid. Blocking of these groups can be accomplished by conventional methods known to those skilled in the art.

In the process of this invention, it is desirable to use a catalyst to promote the esterification reaction. Conventional esterification or transesterification catalysts, which are solid, liquid or a combination of a solid and a liquid, can be used in the process of this invention. Typical catalysts include sulfuric acid, sulfonic acids, ion exchange resins, mineral acids, acidic clays, certain metal compounds and supported catalyst. The sulfonic acid catalysts include, but are not limited to, para-toluene sulfonic acid, benzene sulfonic acid and derivatives thereof, and methanesulfonic acid. The ion exchange resins are preferably those resins having sulfonic acid functionality such as AMBERLYST® A-15 available from Rohm & Haas Company, DOWEX®-type or other resins which also contain sulfonic acid functionality. Mineral acids include, but are not limited, to sulfuric acid. Metal compounds, such as tin, may also be used as a catalyst in the present invention. Examples of these metal compounds include, but are not limited to, dibutyl tin dilaurate. In addition, supported catalyst can be used, such as an acid treated K-10 Montomorrilonite. The catalyst is generally used in an amount in the range of about 0.005 wt. % to about 10 wt. % based on the weight of the reactants in the reaction mixture and will vary depending on the effectiveness of catalyst and, for solid catalyst, the effective concentration of catalytic sites present.

Polymerization inhibitors may also be used in the process of the present invention. These inhibitors, sometimes also called stabilizers, help retard or prevent the polymerization of the reactants during the reaction process and prevent or minimize the further reactions or degradation of the products produced by the microwave heating process of the present invention. The inhibitors are typically present at the start of the reaction process, typically being present in the (meth) acrylic acid reactant and/or the inhibitors can be additionally added before, during, and/or after the reaction process has taken place. Conventional polymerization inhibitors which can be used in the present invention include quinone-type inhibitors, such as hydroquinone, methylether of hydroquinone and various other substituted quinones known in the art, certain copper containing materials, such as copper hydroxide, copper oxide, and copper carbonates, other known stabilizers such as phenothiazine, methylene blue and many of those stabilizers mentioned in U.S. Pat. No. 4,053,504 to Rosenkranz et al., U.S. Pat. No. 3,899,740 to Broussard et al., and U.S. Pat. No. 4,059,721 to Rosenkranz et al., each incorporated by reference. Certain salts of nitroso products, such as aluminum or ammonium salts of N-nitrosophenylhydroxylamine, manufactured by Wako Chemical, are also useful inhibitor system components. These stabilizers can generally be used in combination with air (oxygen), in combination with one another, or they can be used alone, although their effectiveness may be impacted by the conditions (oxygen, inert gas, temperature, etc.) which are present with them. The amount of the polymerization inhibitor added to the reaction mixture is any amount conventionally used in the art. Typically, the polymerization inhibitor is added in an amount up to 3.0 parts by weight based on the weight of the (meth)acrylic acid in the reaction mixture. In the microwave heating process of the present invention, the polymerization inhibitors are especially present in an amount up to 30,000 ppm, based on the weight of the (meth)acrylic acid in the reaction mixture, preferably present in an amount of about 500 ppm, up to about 10,000 ppm.

It is desirable to remove water, volatiles and/or other generated by-products from the reaction mixture to achieve the optimum degree of desired esterification. However, it is not critical to the present invention to remove water or the by-products to successfully produce (meth)acrylate esters using microwave energy. When water is removed, optimum results can be achieved using microwave energy as the heating source. Any conventional water removing technique known to those skilled in the art can be used, and may either take place within the microwave containment zone (provided it is compatible with microwave application) or externally to the microwave containment area, or a combination of both.

Applicable water removal or by-product removal techniques include, but are not limited to, sweeping the vapor area, sparging the reaction mixture, or doing both with a gas or gas mixture which is compatible with the microwave energy and the stability of the reaction mixture and the raw materials. Preferably, microwave inert gases such as non-polar gases should be used. Generally, non-polar gases, for example, oxygen, carbon dioxide, argon, helium and nitrogen or mixtures thereof, as well as air, are very effective in sparging the reaction mixture and choice is determined by various factors including, but not limited to cost, availability, compatibility with inhibitor system, etc. These non-polar gases are not significantly affected by microwaves and thus play only transport and/or inhibition roles. Air can also be used as a sparging gas and is particularly suitable when quinone-type inhibitors or other oxygen-activated inhibitors are present.

In addition, methods including physical adsorption, removal of liquid water or water vapor via known methods can also be used, either within the microwave cavity or external to the cavity as in a continuous recycle loop where drying of the reaction mixture occurs outside of the microwave containment cavity and the dried reactant mixture is returned to the microwave zone for further reaction. Hydroscopic and/or adsorptive agents such as anhydrous calcium sulfate (e.g., DRIERITE® or molecular sieves, water reactive materials such as phosphorous pentoxide and barium oxide are all effective means which can be used to remove water from the reaction mixture vapor with or without the presence of a sparge gas to assist the water transport. Further, evaporation under atmospheric or vacuum conditions, with or without the aid of an azeotroping agent, such as hydrocarbon solvent or an excess of reactant, e.g., the (meth)acrylic acid or polyol or an adsorptive drying agent, can also be used as an effective water removal method. The evaporation methods can also include pervaporation/membranes processes, using materials such as NAFION®, or other membranes, known in the art of membrane technology.

The microwave energy can be continuously or intermittently applied to the reaction mixture. It is desirable to control the amount of microwave energy applied to the reaction to prevent overheating of the reaction mixture bulk temperature, which will in turn minimize or prevent the undesirable polymerization of the (meth)acrylate esters or polyesters (meth)acrylates. The temperature of the reaction mixture, however, must be sufficiently high enough to promote the reactivity of the starting material to form the final products. Methods of controlling the input of microwave energy to the reaction mixture include pulsing the microwaves, and/or using reduced power for heating.

A first method of controlling the bulk temperature of the reaction mixture is to pulse the application of the microwaves. This can be accomplished by applying microwaves for a period of time, followed by a period of time where no microwaves are applied to the reaction mixture. During the periods of time when no microwaves are being applied instantaneously ceases the energy input into the system and allows the reaction mixture to equilibrate to a temperature state via conductive heating within the reaction mixture only. Agitation may or may not also be supplied by various means.

A second method of controlling the reaction mixture temperature is to vary and/or reduce the power of the microwaves being applied to the reaction mixture. By reducing the power of the microwaves, the microwaves can be continuously applied to the reaction mixture while minimizing and controlling the problem of overheating of the bulk reaction mixture.

A third method of controlling the reaction temperature is to use a combination of the first and second methods stated above.

A better method for controlling the temperature of the reaction mixture is to continuously monitor the temperature of the reaction mixture by using a probe in the reaction vessel. This probe then provides data to a computer or an operator which controls the power of the microwaves or amount of time the microwaves are applied to the reactants in the reaction vessel. The computer or operator then makes the necessary adjustments to the microwave power being applied to the reaction mixture so as to control the bulk temperature of the reaction mixture.

The reactants and chemical components used in the microwave heating process of the present invention can be either premixed prior to introduction into the reaction zone or reaction vessel, simultaneously fed to the reaction zone or reaction vessel as separate streams, or various components can be combined in a single stream while other components are fed in a different stream to the reaction vessel or reaction zone. The method of combining the reactants of the reaction mixture is not critical, so long as the (meth)acrylic acid is mixed with a polymerization inhibitor prior to any significant microwave exposure. In addition, the process can be carried out in a batch process, a semi-continuous batch process, or a continuous process.

During the reaction, the contents of the reactor can be stirred or agitated. However, stirring or agitating the reaction is not critical to the invention, but may result in more even-heat distribution as a result of microwave application. Conventional stirring or agitation methods can be used, such as using a magnetic stirrer. Other known stirring methods, which include, but are not limited to, a stirring rod which penetrates the bottom or top of the reaction vessel and the rod is inert or reflective to microwave energy, can also be used to stir the mixture. In addition, the stirring rod is constructed in such a way that microwaves will not escape the reaction zone. When a gas sparge is used, the gas passing through the reactor will also act to agitate the contents of the reactor. Again, it is preferred that the gas is a microwave inert non-polar gas. Using a turntable in the microwave is also an effective method of agitating the container of the reactant mixture in the reactor, thereby minimizing hot spots and equilibrating exposure to the microwaves. In addition, manual agitation can also be used, provided provisions are made for microwave containment during the operation or the operation occurs when microwave delivery is not taking place.

Generally, the reaction mixture is exposed to microwave duty cycles for a period of time between 30 seconds and 300 minutes, preferably between 1 and 240 minutes, and more preferably between 1 and 30 minutes. This period of time will vary depending on the wattage, power of the microwave source used in the process, as well as reaction vessel configuration, quantity of sample present and other equipment factors, including delivered microwave efficiency and frequency. Preferably, the wattage of the microwave is such that a conversion of 5–100% of the hydroxy functionality is obtained in a time period of about 1 to 30 minutes. The preferred time period for conversion is in the about 5 to 30 minutes range while achieving at least 85% reaction of the hydroxy group functionality. This time period will vary depending on the size of the reactor or the contents of the reactor as well as the equipment characteristics and specifications as noted above.

In addition, the reaction mixture can be held at an elevated temperature with intermittent or continuous microwave impingement for a given period of time to achieve at least 5% conversion of the hydroxy groups to esters as a result of microwave energy input and resulting inductive heating. Preferably, the reaction mixture is held at an elevated temperature for a sufficient amount of time to achieve at least 50% conversion of the hydroxy groups and most preferably at least 85% conversion of the hydroxy groups. The microwave energy is applied to the reaction mixture so that the bulk temperature of the reaction mixture is maintained at a temperature higher than room temperature, for example, 30° C., usually in the range of about 50° C. to about 180° C. Preferably, the temperature of the reaction mixture is maintained in the range of about 110° C. to 150° C.

The process of this invention can take place under vacuum, at atomspheric pressure or above atomspheric pressure. It can be advantageous to use a vacuum if one of the reactants is sensitive to high temperatures. Likewise, it can be advantageous to use pressure if a given reactant is too volatile to achieve the desired reaction temperture without distilling from the reaction mixture. However, the most convenient method is to use about atmospheric pressure.

The process of this invention can also be performed in a vessel which has internal cooling. Internal cooling is provided by placing a material into the reaction mixture which is inert to or reflects microwaves, hence, the material does not increase in temperature due to the exposure to microwaves. However, the material does increase in temperature via thermal conduction from the reaction solution. Examples of material which can be used as the internal cooling material include, but are not limited to a properly grounded stainless steel cooling finger, which reflects but does not absorb microwaves, with a circulating coolant such as chilled water or other liquid having a high heat capacity, a cooled gas such as carbon dioxide, or dry ice solid. This internal cooling can be provided by cycling the cooling material through single or multiple tubes which are inert to microwaves and present in the reaction mixture. This method is also effective to control the temperature of the reaction mixture. External cooling of the reactant mixture is also an option for continuously recirculated reactant processing, but not a specific requirement for the particular invention.

The process of the present invention can be run in a batch, step-wise batch semi-continuous process, or continuous mode. In the step-wise batch process, the exposure to the microwaves of the reaction mixture can be accomplished with or without an intermediate cooling step. Recycling of the mixture through the reaction zone can be done in a continuous or semi-continuous method.

The final products produced by the process of this invention can be recovered and isolated from the reaction mixture using conventional techniques known in the art. Included in these techniques is dilution in solvent and water washing, neutralization, solvent removal and distillative techniques or any other separation techniques known in the art.

Solvents, while not a preferred component of this invention, can also be used in the microwave heating process of this invention. Both polar solvents and non-polar solvents can be used. Polar solvents will be activated by the application of microwaves and thus contribute to heating of the reactants via conductive processes, while non-polar solvents will not be activated by the application of microwaves to the reaction mixture and primarily serve only as a heat conductive medium. The solvents, in both cases, can serve to assist in water removal through azeotroping and control the bulk reaction temperatures through reflux. However, it is preferred that solvents are not used in the present invention since the introduction of solvents introduces the problems associated with solvent removal and other solvent properties such as containment and safety issues of exposure, handling, flammability and the like. Using a solventless process has the advantages of improved yield, efficiency, minimal waste disposal, lower material cost, etc. In addition, the products of the present invention produced without a solvent have improved safety due to the absence of flammable hydrocarbon solvents typically used in the process. An additional advantage sometimes seen is improved quality in product properties such as color, byproducts, and the like. When a solventless process is used, it is preferred that at least one of the reactants is responsive to microwave energy. The (meth) acrylic acid reactants, hydroxy functional reactants and catalysts used in this invention are, or can be, polar, hence, are microwave active. This means that at least one of the reactants is heated by microwave energy when the reactant is exposed to microwave energy.

The process of the invention can be realized with a sparge or without a sparge system. The principle of the process without a sparge system for water removal assistance can be summarized according to the following:

A mixture of the following: 0.5 to 10 equivalents of (meth)acrylic acid, 1 equivalent of hydroxyl, as a monohydroxy or polyhydroxy compound, 0.05 to 10 wt. %, based on the reaction mixture, of a catalyst, and 50 to 30,000 ppm, based on the weight of the (meth)acrylic acid, of a polymerization inhibitor are added to a flask or other microwave-inert reaction vessel. The mixture of the reactants is placed into a typical kitchen variety microwave oven, or more preferably, a microwave oven specifically designed for laboratory synthesis. This microwave energy may be delivered either proportionally in a continuous manner or pulsed at certain frequency for specified amounts of time to deliver the microwave energy to the sample. The reaction vessel is attached to a receiving vessel either within the microwave chamber, as in the case of a kitchen-type microwave, or an external chamber, in the case of laboratory or other specially designed equipment, and this receiving vessel is cooled by dry ice or other means to trap water and generated volatiles. The contents of the reaction vessel are heated in the microwave containment chamber for a period of time at a given power in a manner consistent with the microwave equipment's power delivery capabilities. The contents of the reaction vessel are shaken manually or agitated via other means and can be heated additional time as required for the intended reaction. This treatment cycle can be varied depending upon the work being done. A sample is periodically withdrawn from the reaction mixture and is analyzed by gas chromatography or other means to determine the degree of completeness of the reaction based upon such attributes as the disappearance of hydroxy-containing product signals, and/or appearance of signals due to the newly formed (meth)acrylate products, and comparison to standard product or starting materials. The reaction mixture is then further subjected to microwave exposure until the desired degree of reaction completeness is achieved or a target reaction time/exposure level is reached.

Similarly, the principles of the inventive process with a sparge system can be summarized according to the following:

A mixture of the following: 0.5 to 10 equivalents of (meth)acrylic acid, 1 equivalent of hydroxyl, as a monohydroxy or polyhydroxy compound, 0.05 to 10 wt. %, based on the reaction mixture, of a catalyst, and 50 to 30,000 ppm, based on the weight of the (meth)acrylic acid, of a polymerization inhibitor are added to a flask or other microwave-inert reaction vessel. The mixture of the reactants is placed into a typical kitchen variety microwave oven, laboratory or other grade microwave oven adapted for synthesis. The reactor vessel containing the reactants is attached to a receiving vessel, which is cooled by dry ice or other appropriate means to trap water and generated volatiles. Another test tube or flask is filled with dry ice or equipped for gas sparge and connected to the reactor with a tube extending into the vapor space or into the reaction mixture in the reactor vessel. As the dry ice vaporizes or other gas flows through this connection, the carbon dioxide or other gas passes through (sparges) the vapor space or the liquid contents of the reactor, thereby agitating the contents, if the tube is subsurface in the reactants, and also acts to remove water and volatiles from the reactor via entrainment. The entire reaction train (dry ice vessel, reactant vessel, and receiver vessel) can be placed in the microwave containment chamber for a given period of time at a given power, or in the case of an appropriately designed laboratory microwave equipment, the dry ice sparge tube or other gas source can be located outside the microwave oven and run into the reaction vessel via appropriate tubing. Likewise, the collection vessel can be located either inside the microwave containment chamber or external to the containment chamber, connected by additional inert tubing and connections. The contents of the reaction vessel can be agitated by shaking manually or via other stirring processes. This treatment can be varied depending upon the experiment being conducted. A sample is periodically withdrawn from the reaction mixture and is analyzed by gas chromatography to determine the degree of completeness of the reaction based upon the disappearance of hydroxy-containing product signals and/or appearance of discernable product responses in the gas chromatography or by other analytical techniques appropriate to the experiment being conducted. The reaction mixture is then further subjected to microwave exposure as described above for the no sparge system until the desired degree of reaction completeness is achieved or until a certain target exposure time is achieved.

The above summarized process of the invention may be applied to a single step batch process, a multiple batch (semi-continuous batch) process, a continuous process or a combination of these. In a semi-continuous or continuous process, the reactants and/or reaction mixture is charged and/or circulated by methods known in the art including but not limited to peristaltic pump, pressurization, or other conventional circulation techniques. The sample can be either recycled multiple times through the microwave zone, or conducted in a single pass through the zone, depending on results being targeted. Cooling may be included or not at various steps in the circulation process, depending on target results. Reactants may be added continuously, stepwise, or as individual or mixtures during the process.

EXAMPLES

In the following Examples, two different microwaves are used. These microwave ovens used in the Examples are unmodified commercial ovens, each having a microwave frequency generation of 2450 MHz±50 MHz. The following specifications were measured with each particular oven used in the Examples.

500.0 gms of deionized water at room temperature was added to a 1000 ml Pyrex laboratory beaker. The temperature of the water was measured using a thermometer. The beaker was placed in the center of the respective oven and exposed to a 2 minute uninterrupted cycle at the noted power setting. Immediately upon completion of the 2 minute heating, the sample was removed from the oven and the maximum temperature measured using the thermometer was recorded. Fresh samples were used for each test. The results for each microwave oven is as follows:

Sears® Oven (1000 watt rated power)
- 100% power: water temperature increases from 24° C. to 62° C.
- 50% power: water temperature increases from 24° C. to 45° C.
- 20% power: water temperature increases from 24° C. to 35° C.

Litton® Oven (800 watt rated power)
- 100% or Full power: water temperature increases from 24° C. to 58° C.
- 50% or #5 power: water temperature increases from 24° C. to 40° C.
- 20% or #2 power: water temperature increases from 24° C. to 30° C.

Example 1

A mixture of 7.3 g of methacrylic acid (84.8 mmoles), 5.0 gms of 1,6-hexanediol (42.3 mmoles), 0.1 gms of phenothiazine, and 0.6 gms of methanesulfonic acid (70% solution in water) are combined in a test tube which is configured to trap any volatile. The equipment set-up is described above. The mixture of the reactants in the test tube is placed into the Sears® Kitchen Microwave Oven. The contents of the test tube are heated in the microwave oven for 30 seconds at 20% power. The contents of the test tube are shaken manually and heated again for 30 seconds at 20% power. Eighteen additional heating/agitation cycles of 20-sec intervals of heating at 20% power followed by agitation were conducted. After a total of 7 minutes cumulative microwave exposure (27 minutes total elapsed time) a sample of the mixture was collected and analyzed by gas chromatography (GC) for product composition. Based upon GC peak analysis (area % values), the product contained 74.2% 1,6-hexanediol dimethacrylate, 22.2% 1,6-hexanediol monomethacrylate, and 1.3% 1,6-hexanediol along with some other minor peaks.

Example 2

A mixture of 7.3 g of methacrylic acid (84.8 mmoles), 2.5 gms of 1,6-hexanediol (21.1 mmoles), 0.1 gms of phenothiazine, and 0.6 gms of methanesulfonic acid (70% solution in water) are combined in a test tube. The mixture of the reactants in the test tube is placed into the Sears® Kitchen Microwave Oven. The contents of the test tube are heated in the microwave oven for 30 seconds at 20% power. The contents of the test tube were shaken manually and heated again for 30 seconds at 20% power. Eighteen additional heating/agitation cycles of 20-sec intervals of heating at 20% power followed by agitation were conducted. After a total of 7 minutes cumulative microwave exposure (27 minutes total elapsed time) a sample of the mixture was collected and analyzed by gas chromatography for product composition. Based upon GC peak analysis (area % values), the product contained 90.7% 1,6-hexanediol dimethacrylate, 6.3% 1,6-hexanediol monomethacrylate, along with some other minor peaks.

Control Example 1 (no catalyst)

7.99 gms of a mixture containing 43.7 gms of methacrylic acid (508 mmoles), 30 gms of 1,6-hexanediol (254 mmoles), 0.1 gms of phenothiazine, 0.1 gms hydroquinone and no catalyst is placed in a test tube. The mixture of the reactants in the test tube is placed into the Sears® Kitchen Microwave Oven. The contents of the test tube are heated in the microwave oven for 30 seconds at 20% power. The contents of the test tube were shaken manually and heated again for 30 seconds at 20% power. Eighteen additional heating/agitation cycles of 20-sec intervals of heating at 20% power followed by agitation were conducted. After a total of 7 minutes cumulative microwave exposure (17 minutes total elapsed time) a sample of the mixture was collected and analyzed by gas chromatography for product composition. Based upon GC peak analysis (area % values), the product contained less than 0.5% 1,6-hexanediol dimethacrylate, 3.5% 1,6-hexanediol monomethacrylate, and 93.4% 1,6-hexanediol starting polyol.

Example 3

8.00 gms of a mixture containing 43.7 gms of methacrylic acid (508 mmoles), 30 gms of 1,6-hexanediol (254 mmoles), 0.1 gms of phenothiazine and 0.1 gms hydroquinone is placed in a test tube. Then 0.8058 gms of AMBERLYST® A-15 sulfonic acid ion exchange resin catalyst is added to the test tube to form the reaction mixture. The reaction mixture in the test tube is placed into the Sears® Kitchen Microwave Oven. The contents of the test tube are heated in the microwave oven for 30 seconds at 20% power. The contents of the test tube were shaken manually and heated again for 30 seconds at 20% power. Eighteen additional heating/agitation cycles of 20-sec intervals of heating at 20% power followed by agitation were conducted. After a total of 7 minutes cumulative microwave exposure (17 minutes total elapsed time) a sample of the mixture was collected and analyzed by gas chromatography for product composition. Based upon GC peak analysis (area % values), the product contained 22.1% 1,6-hexanediol dimethacrylate, 59.5% 1,6-hexanediol monomethacrylate, and 15.2% 1,6-hexanediol starting polyol along with other minor peaks.

Example 4

8.04 gms of a mixture containing 43.7 gms of methacrylic acid (508 mmoles), 30 gms of 1,6-hexanediol (254 mmoles), 0.1 gms of phenothiazine and 0.1 gms hydroquinone is placed into a test tube. Then 0.4230 gms of para-toluenesulfonic acid monohydrate are added to the test tube for the reaction mixture. The reaction mixture in the test tube is placed into the Sears® Kitchen Microwave Oven. The contents of the test tube are heated in the microwave oven for 30 seconds at 20% power. The contents of the test tube were shaken manually and heated again for 30 seconds at 20% power. Eighteen additional heating/agitation cycles of 20-sec intervals of heating at 20% power followed by agitation were conducted. After a total of 7 minutes cumulative microwave exposure (17 minutes total elapsed time) a sample of the mixture was collected and analyzed by gas chromatography for product composition. Based upon GC peak analysis (area % values), the product contained 64.9% 1,6-hexanediol dimethacrylate, 30.5% 1,6-hexanediol monomethacrylate, and 2.7% 1,6-hexanediol starting polyol along with other minor peaks.

Example 5

8.10 gms of a mixture containing 43.7 gms of methacrylic acid (508 mmoles), 30 gms of 1,6-hexanediol (254 mmoles), 0.1 gms of phenothiazine, 0.1 gms hydroquinone is placed in a test tube. Then 0.4200 gms of concentrated sulfuric acid are added to the test tube to form the reaction mixture. The reaction mixture in the test tube is placed into the Sears® Kitchen Microwave Oven. The contents of the test tube are heated in the microwave oven for 30 seconds at 20% power. The contents of the test tube were shaken manually and heated again for 30 seconds at 20% power. Eighteen additional heating/agitation cycles of 20-sec intervals of heating at 20% power followed by agitation were conducted. After a total of 7 minutes cumulative microwave exposure (17 minutes total elapsed time) a sample of the mixture was collected and analyzed by gas chromatography for product composition. Based upon GC peak analysis (area % values), the product contained 78.9% 1,6-hexanediol dimethacrylate, 16.2% 1,6-hexanediol monomethacrylate, and 0.5% 1,6-hexanediol starting polyol along with other minor peaks.

Example 6

24.2 gms of acrylic acid (336 mmoles), 10 gms of trimethylolpropane (74.5 mmoles), 0.1 gms of 4-methoxyphenol, 0.8 gms K-10 Montomorrilonite clay and 0.8 gms para-toluenesulfonic acid monohydrate are combined and placed in a 50 ml flask. The mixture of the reactants in the flask is placed into the Litton® Kitchen Microwave Oven. The contents of the flask are heated in the microwave oven for 45 seconds at #5 setting. The contents of the flask were shaken manually and heated again for 15 seconds at #5 setting. Twenty-eight further heating/agitation cycles of 15-sec intervals of microwave heating at #5 setting followed by agitation were conducted. Bulk temperature was measured to be about 134° C. by thermometer at the end of 8 minutes cumulative microwave exposure. After a total of 8 minutes cumulative microwave exposure (35 minutes total elapsed time) a sample of the mixture was collected and analyzed by gas chromatography for product composition. Based upon GC peak analysis (area % values), the product contained 45.6% trimethylolpropane triacrylate, 26.8% trimethylolpropane diacrylate, 6.3% trimethylolpropane monoacrylate, 0.5% trimethylolpropane, 11.8% (total of two GC peaks) higher molecular weight products, along with other minor peaks.

Comparative Example 1

24.2 gms of acrylic acid (336 mmoles), 10 gms of trimethylolpropane (74.5 mmoles), 0.1 gms of 4-methoxyphenol, 0.8 gms K-10 Montomorrilonite clay and 0.8 gms para-toluenesulfonic acid monohydrate are combined and placed in a 50 ml flask. The mixture of the reactants in the test tube is placed into an oil bath heated to 134° C. and stirred via a magnetic stirrer. The mixture was held in the bath for 35 minutes total time at a temperature of about 134° C. oil temperature. After a total of 35 minutes a sample of the mixture was collected and analyzed by gas chromatography for product composition. Based upon GC peak analysis (area % values), the product contained 39.9% trimethylolpropane triacrylate, 32.5% trimethylolpropane diacrylate, 9.6% trimethylolpropane monoacrylate, 0.6% trimethylolpropane, 9.9% (total of two GC peaks) higher molecular weight products, along with other minor peaks.

Example 7

About 4 gms of a mixture (containing 7.7 gms of acrylic acid (107 mmoles), 6.0 gms 1,6-hexanediol (50.8 mmoles), about 0.05 gms of 4-methoxyphenol, 0.4 gms K-10 Montomorrilonite clay and 0.35 gms para-toluenesulfonic acid monohydrate) is placed in a test tube. The mixture of reactants in the test tube is placed into the Litton® Kitchen Microwave Oven. The contents of the test tube are heated in the microwave oven for 40 seconds at full power. The contents of the flask were shaken manually and heated again for 20 seconds at 100% power. Twelve more heating/agitation cycles of 20-sec intervals of microwave heating at 100% power followed by agitation were conducted to a total microwave exposure time of 4 minutes. A sample of the mixture was collected and analyzed by gas chromatography for product composition. Based upon GC peak analysis (area % values), the product contained 36.8% 1,6-hexanediol diacrylate, 45.4% 1,6-hexanediol monoacrylate, 11.0% 1,6-hexanediol along with other minor peaks.

Example 8

16.1 gms of acrylic acid (223 mmoles), 10 gms of trimethylolpropane (74.5 mmoles), 0.1 gms of 4-methoxyphenol and 0.2 gms para-toluenesulfonic acid monohydrate are combined and placed in a test tube. The reaction mixture in the test tube is placed into the Litton® Kitchen Microwave Oven. The contents of the test tube are heated in the microwave oven for 30 seconds at a # 2 power setting. The contents of the flask were shaken manually and heated again for 15 seconds at the #2 power setting. Thirty-seven more heating/agitation cycles of 15-sec intervals of microwave heating at the #2 power setting followed by agitation were conducted for a total microwave exposure of 10 minutes (total elapsed time of 29 minutes). A sample of the mixture was collected and analyzed by gas chromatography for product composition. Based upon GC peak analysis (area % values), the product contained 30.4% trimethylolpropane triacrylate, 39.3% trimethylolpropane diacrylate, 19.5% trimethylolpropane monoacrylate, 2.5% trimethylolpropane, 8.0% (total of two GC peaks) higher molecular weight products, along with other minor peaks. No gel was observed.

Example 9

3.5 gms of acrylic acid (48.5 mmoles) with various levels of copper(I) oxide, 2.0 gms of trimethylolpropane (14.9 mmoles) and 0.1 gms 70% methanesulfonic acid (aqueous solution) are combined and placed in a test tube. The reactants mixture in the test tube is placed into the Sears® Kitchen Microwave Oven. The contents of the test tube are heated in the microwave oven at 20% power setting and checked every minute for gel formation at which time the sample was manually shaken before being again exposed for the next minute to microwave treatment.

Results:

zero $Cu_2O$—gelled in less than 1 minute exposure, 100 ppm $CU_2O$ (based upon acrylic acid charge)—about 6 minutes before gelling occurs 250 ppm $CU_2O$ (based upon acrylic acid charge)—about 12 minutes, the mixture begins to thicken/gel.

500 or 1000 ppm $CU_2O$ (based up on acrylic acid charge)—no gelling seen at 12 minutes cumulative microwave exposure

Example 10

3.5 gms of acrylic acid (48.6 mmoles) containing 1000 ppm copper(I)oxide, 1.0 gms of trimethylolpropane (7.5 mmoles), 0.1 gms of methanesulfonic acid (70% solution in water) are combined and placed in a test tube. An additional test tube is filled with powdered dry ice and connected to the tube holding the reaction mixture. This additional test tube supplies carbon dioxide sparge to the reaction tube as the dry ice vaporizes. The reaction mixture tube is also connected via a separate tube to a receiver tube which is surrounded externally by dry ice (vapor trap). The sparge, reactor, and trap tubes are all placed into the Sears® Kitchen Microwave Oven. The setup is heated in the microwave oven for 30 seconds at 20% power. The contents of the test tube were shaken manually and heated again for 30 seconds at 20% power. Eighteen additional heating/agitation cycles of 30 sec intervals of microwave heating at 20% power followed by agitation were conducted for a total microwave exposure of 10 minutes (total elapsed time of 22 minutes). A sample of the mixture was collected and analyzed by gas chromatography for product composition. Based upon GC peak analysis (area % values), the product contained 51.2% trimethylolpropane triacrylate, 12.5% trimethylolpropane diacrylate, 2.5% trimethylolpropane monoacrylate, less than 0.5% trimethylolpropane, 23% (total of two GC peaks) higher molecular weight products, along with other minor peaks.

Example 11

A mixture of 15.1 gms of acrylic acid (209.5 mmoles) saturated with copper(I)oxide inhibitor, 10 gms of tripropylene glycol (52.0 mmoles), 0.1 gms of phenothiazine, 0.1 gms hydroquinone and 0.77 gm methanesulfonic acid (70% solution in water) catalyst are combined in a test tube. An additional test tube is filled with powdered dry ice and connected to the tube holding the reaction mixture. This additional test tube supplies carbon dioxide sparge to the reaction tube as the dry ice vaporizes. The reaction mixture tube is also connected via a separate tube to a receiver tube which is surrounded externally by dry ice (vapor trap). The sparge, reactor, and trap tubes are all placed into the Sears® Kitchen Microwave Oven. The setup is heated in the microwave oven for 30 seconds at 20% power. The contents of the test tube were shaken manually and heated again for 30 seconds at 20% power. Twenty-eight more heating/agitation cycles of 30 sec intervals of microwave heating at 20% power followed by agitation were conducted. After a total of 15 minutes cumulative microwave exposure (36 minutes total elapsed time) a sample of the mixture was collected and analyzed by gas chromatography for product composition. Based upon GC peak analysis (area % values), the product contained less than 0.5% Tripropylene glycol, 5.5% tripropylene glycol monoacrylate, 55.5% tripropylene glycol diacrylate, 20.3% higher molecular weight acrylates (sum of two peaks) and other minor product peaks.

Example 12

A mixture of 20.0 gms of acrylic acid (277.5 mmoles) 0.03 gms copper(l)oxide inhibitor, 10 gms of propoxylated glycerin (35.7 mmoles), and 0.77 gms methanesulfonic acid (70% solution in water) catalyst are combined in a test tube. An additional test tube is filled with powdered dry ice and connected to the tube holding the reaction mixture. This additional test tube supplies carbon dioxide sparge to the reaction tube as the dry ice vaporizes. The reaction mixture tube is also connected via a separate tube to a receiver tube which is surrounded externally by dry ice (vapor trap). The sparge tube, reactor tube, and trap tube are all placed into the Sears® Kitchen Microwave Oven. The setup is heated in the microwave oven for 30 seconds at 20% power setting. The contents of the test tube were shaken manually and heated again for 30 seconds at 20% power. Twenty-eight heating/agitation cycles of 30 sec intervals of microwave heating at 20% power followed by agitation were conducted. After a total of 15 minutes cumulative microwave exposure (about 23 minutes total elapsed time) a sample of the mixture was collected and analyzed by gas chromatography for product composition. Based upon GC peak analysis (area % values), the product contained 47.5±% triacrylate, 11.4±% diacrylate, and various other unidentified product peaks.

Example 13

A mixture of 3.0 9 of acrylic acid (41.6 mmoles), 5.0 gms of an about 45/55 ratio of octanol and decanol (ALFOL® 810) available from Vista Chemical (about 34 mmoles monoalcohols), 0.01 gm of copper(I)oxide, and 0.4 gms of methanesulfonic acid (70% solution in water) is combined in a test tube. The mixture of the reactants in the test tube is placed into the Sears® Kitchen Microwave Oven. The contents of the test tube are heated in the microwave oven for 30 seconds at 20% power. The contents of the test tube were shaken manually and heated again for 30 seconds at 20% power. Eighteen additional heating/agitation cycles of 20 sec intervals of heating at 20% power followed by agitation were conducted. After a total of 7 minutes cumulative microwave exposure (11 minutes total elapsed time) a sample of the mixture was collected and analyzed by gas chromatography for product composition. Based upon peak analysis (area % values), the product contained 4.4% alcohol (C8±C10), and 93.5% monoacrylate (C8 and C10 mixture), along with some other minor peaks.

Example 14

A stock solution mixture composed of 25.0 gm trimethylolpropane (186 mmoles), 40.3 gms of acrylic acid (559 mmoles) containing about 200 ppm of 4-methoxyphenol (as a stabilizer) and 3.3 gms of an aqueous 70% methanesulfonic acid solution was prepared. Six samples of about 10 gms each were placed into separate test tubes. To each test tube was added about 0.005 gms of various inhibitors (about 500 ppm). The reaction mixture tube is also connected via a separate tube to a receiver tube which is surrounded externally by dry ice (vapor trap). The aliquots were then placed in the Sears® Microwave Oven and exposed for 30 second intervals at 20% power. Following each exposure, the sample was manually shaken to agitate and approximate time to gellation was noted in 30 sec. increments.

Results were as follows:

| Inhibitor | Approximate seconds of microwave prior to gelling |
| --- | --- |
| no added inhibitor [control] | less than 90 sec |
| BHT | 120 sec |
| hydroquinone | 120 sec |
| 2,5-di-tertbutylhydroquinone | 240 sec |
| Methylene blue | 600 sec |
| copper(1)oxide | greater than 600 sec |

What is claimed is:

1. A process for preparing an acrylate ester, a methacrylate ester, a polyester acrylate or a polyester methacrylate comprising reacting acrylic or methacrylic acid with a monohydroxy containing compound or polyhydroxy containing compound in a reaction vessel, in the presence of a catalyst and a polymerization inhibitor, using microwave energy as the heating source, wherein the reaction takes place in the absence of a solvent.

2. The process of claim 1, wherein water and/or volatiles produced by the reaction are removed from said reaction vessel and/or are trapped.

3. The process of claim 1, wherein water and/or volatiles produced by the reaction are not removed from the reaction vessel.

4. The process of claim 2, wherein the water and/or volatiles are removed by sparging the reaction vessel with microwave-inert gas.

5. The process of claim 4, wherein the microwave-inert gas is selected from the group consisting of carbon dioxide, air, argon, helium, nitrogen and mixtures thereof.

6. The process of claim 1, wherein the microwave energy is intermittently applied to the reaction vessel by pulsing the microwaves.

7. The process of claim 1, wherein the microwave energy is applied continuously to the reaction vessel.

8. The process of claim 1, wherein the contents of the reaction vessel are heated by microwave energy and held at an elevated temperature for a period of time to achieve at least 5% conversion of the hydroxy groups.

9. The process of claim 8, wherein the contents of the reaction vessel are heated and held at a temperature between about 30° C. and about 180° C.

10. The process of claim 9, wherein the contents of the reaction vessel are heated to a temperature between about 110° C. and about 150° C.

11. The process of claim 1, wherein the contents of the reaction vessel are subjected to microwave energy for a period of time between about 30 seconds and about 300 minutes.

12. The process of claim 11, wherein the period of time is between about 1 and 30 minutes.

13. The process of claim 1, wherein the contents of the reaction vessel are subjected to microwave energy for a period of time sufficient to achieve a conversion of about 5.0 to 100% of the starting hydroxy functionality to the acrylate ester, methacrylate ester, polyester acrylate or polyester methacrylate.

14. The process of claim 1, wherein the reaction mixture is agitated during the application of the microwave energy.

15. The process of claim 14, wherein the reaction mixture is agitated by sparging the reaction mixture with an inert gas.

16. The process of claim 1, wherein at least one of the reactants is active to microwave energy.

17. The process of claim 1, further comprising the steps of recovering the monoester or polyester from the reaction mixture.

18. The process of claim 1, wherein the reactants are simultaneously fed to the reactor.

19. The process of claim 1, wherein the reactants are premixed prior to addition of the reactants to the reactor.

20. The process of claim 1, wherein the catalyst component is present in reaction vessel in an amount of 0.005 to 10.0 wt. %, based on the total weight of the reactants in the reaction mixture.

21. The process of claim 1, wherein the polymerization inhibitor is present in an amount up to 30,000 ppm, based on the weight of the acrylic or methacrylic acid reactant.

22. The process of claim 1, wherein the polymerization inhibitor is selected from the group consisting of hydroquinone, methylether of hydroquinone, phenothiazine, methylene blue, substituted quinones, copper(1)oxide, copper carbonate, and a combination thereof.

23. The process of claim 1, wherein the reaction is conducted under a vacuum.

24. The process of claim 1, wherein the reaction is conducted at or above atmospheric pressure.

25. A process for preparing an acrylate ester, a methacrylate ester, a polyester acrylate or a polyester methacrylate comprising reacting acrylic or methacrylic acid with a monohydroxy containing compound or polyhydroxy containing compound in a reaction vessel, in the presence of a catalyst and a polymerization inhibitor using microwave energy as the heating source, wherein the reaction vessel has internal cooling provided by a material or through a material, wherein the material removes heat primarily by thermal conduction from the reaction solution and the material is inert to microwave energy or reflects microwaves.

26. The process of claim 25, wherein the material is dry ice, chilled gas, or a non-microwave-adsorbent chamber comprising liquid coolant having a high heat capacity housed within the chamber.

27. The process of claim 1, wherein the monohydroxy containing compounds are selected from the group consisting $C_{1-18}$ linear or branched aliphatic monohydroxy compounds, cycloaliphatic monohydroxy compound and aromatic monohydroxy compounds and the polyhydroxy compounds are polyols having about 2 to about 10 hydroxy groups and 2 to about 36 carbon atoms.

28. The process of claim 27, wherein the monohydroxy containing compounds are selected from the group consisting of methanol, ethanol, cyclohexanol, octanol, and decanol; and the polyhydroxy compounds are selected from the group consisting of cyclohexanediol, butanediol, hexanediol, tripropylene glycol, tetraethyleneglycol, trimethylolpropane, pentaerythritol, ethoxylated trimethylolpropane, propoxylated glycerine, dipentaerythritol, di-trimethylolpropane and triethylene glycol.

29. The process of claim 1, wherein the catalyst is selected from the group consisting of para-toluenesulfonic acid, methanesulfonic acid, sulfonic acid ion-exchange resins, sulfuric acid, and acid clays.

30. The process of claim 4, wherein the reaction is conducted under a vacuum.

* * * * *